(12) United States Patent
Prakash et al.

(10) Patent No.: US 11,833,519 B2
(45) Date of Patent: Dec. 5, 2023

(54) CO-AXIAL PLUNGER BASED HOME MOLECULAR DIAGNOSTICS KIT

(71) Applicant: The Board of Trustees of the Leland Stanford Junior University, Stanford, CA (US)

(72) Inventors: Manu Prakash, San Francisco, CA (US); Anesta Kothari, San Francisco, CA (US); Adam George Larson, San Francisco, CA (US); Shailabh Kumar, Sunnyvale, CA (US); Hazel Soto-Montoya, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 395 days.

(21) Appl. No.: 17/240,767

(22) Filed: Apr. 26, 2021

(65) Prior Publication Data
US 2022/0097073 A1    Mar. 31, 2022

Related U.S. Application Data

(60) Provisional application No. 63/120,401, filed on Dec. 2, 2020, provisional application No. 63/085,664, filed on Sep. 30, 2020.

(51) Int. Cl.
*B01L 3/00* (2006.01)
*B01L 7/00* (2006.01)
*B01L 3/02* (2006.01)

(52) U.S. Cl.
CPC .............. *B01L 7/52* (2013.01); *B01L 3/0217* (2013.01); *B01L 3/5023* (2013.01)

(58) Field of Classification Search
None
See application file for complete search history.

(56) References Cited

U.S. PATENT DOCUMENTS

| 4,640,297 A | * | 2/1987 | Bates | ............... A61B 5/150099 |
| | | | | 73/864.16 |
| 5,124,041 A | | 6/1992 | Sheer | |
| 5,440,940 A | * | 8/1995 | Wilkins | ..................... B01L 3/02 |
| | | | | 422/561 |

(Continued)

FOREIGN PATENT DOCUMENTS

CA             2025261          3/1991

*Primary Examiner* — Brian R Gordon
(74) *Attorney, Agent, or Firm* — LUMEN PATENT FIRM

(57) ABSTRACT

Instrument free "plasticware" is provided that enables multi-step molecular reactions in a diagnostics context. A hollow plunger that is movable within a surrounding tube defines a reaction chamber inside the plunger. By moving the plunger to different positions in the tube, a sample can be collected, then the sample can be washed, and finally the reaction chamber can be sealed to perform diagnostic reactions on the sample. The juxtaposition of large sample collection/washing volume with small reaction volume allows one to conduct a wide range of diagnostic assays including a LAMP (Loop mediated isothermal amplification) based saliva test in a small, portable self-contained device. Applications include Molecular diagnostics for health applications (including COVID19 test), Environmental Monitoring, Disease surveillance, and Veterinary health.

9 Claims, 6 Drawing Sheets

(56) References Cited

U.S. PATENT DOCUMENTS

| | | | |
|---|---|---|---|
| 6,716,187 B1* | 4/2004 | Jorgensen | B01L 3/5021 |
| | | | 604/407 |
| 11,112,405 B1* | 9/2021 | Rai | G01N 33/54366 |
| 11,465,145 B2* | 10/2022 | Scott | G01N 1/18 |
| 2005/0048670 A1* | 3/2005 | Wu | B01L 3/502 |
| | | | 422/550 |
| 2012/0201726 A1 | 8/2012 | Pearcy | |
| 2012/0214251 A1* | 8/2012 | Bonecker | B01F 35/2207 |
| | | | 436/164 |
| 2013/0270173 A1* | 10/2013 | Tortorella | B01L 3/508 |
| | | | 210/416.1 |
| 2014/0322102 A1 | 10/2014 | Pearcy | |
| 2016/0016171 A1 | 1/2016 | Goel | |
| 2018/0089827 A1 | 3/2018 | Holmes | |
| 2018/0220945 A1* | 8/2018 | Sink | A61B 5/150503 |
| 2019/0351420 A1 | 11/2019 | Pearcy | |
| 2021/0080362 A1* | 3/2021 | Lutnesky | B01L 3/502 |
| 2023/0096409 A1* | 3/2023 | Feldman | G01N 1/4077 |
| | | | 73/863.23 |

\* cited by examiner

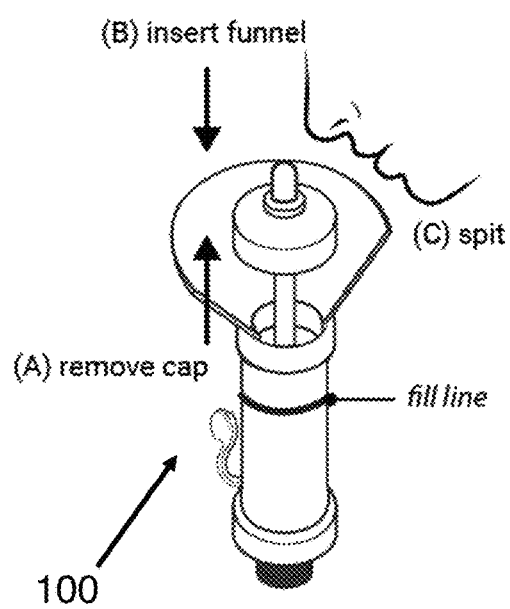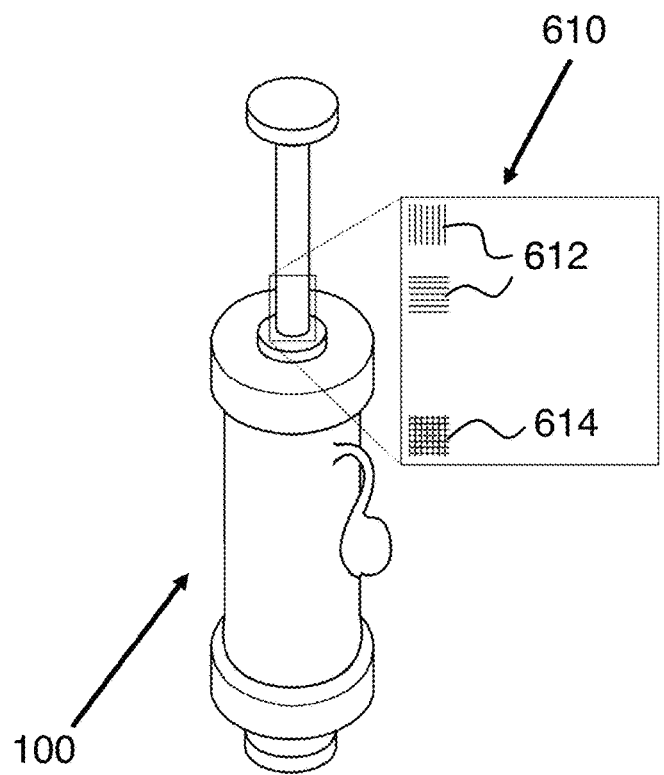
FIG. 6C
FIG. 6D

CO-AXIAL PLUNGER BASED HOME MOLECULAR DIAGNOSTICS KIT

CROSS REFERENCE TO RELATED APPLICATIONS

This application claims the benefit of U.S. provisional patent application 63/085,664, filed on Sep. 30, 2020, and hereby incorporated by reference in its entirety.

This application claims the benefit of U.S. provisional patent application 63/120,401, filed on Dec. 2, 2020, and hereby incorporated by reference in its entirety.

FIELD OF THE INVENTION

This invention relates to home molecular diagnostic methods and kits.

BACKGROUND

Molecular testing has remained limited to lab and well-resourced settings. It is often expensive and requires complex instrumentation which is too complex to be deployed in home settings, both in well-resourced and low-resource settings. Often multiple challenges have to be solved in developing a diagnostics device—including handling of larger volume of sample to capture analytes of interest while still conducting the final reactions such as an isothermal amplification step in a small volume. Furthermore, cross contamination has to be minimized to ensure result from one reaction do not bias future reactions. Finally, the device needs to be mass manufacturable to enable scale-up. Accordingly it would be an advance in the art to provide some or all of these desirable features.

SUMMARY

In this work, a completely instrument free "plasticware" is provided that enables multi-step molecular reactions in a diagnostics context. A hollow plunger that is movable within a surrounding tube defines a reaction chamber inside the plunger. By moving the plunger to different positions in the tube, a sample can be collected, then the sample can be washed, and finally the reaction chamber can be sealed to perform diagnostic reactions on the sample. An exemplary device includes capacity to:
(1) enable inactivation and cell lysis from a given sample, such as saliva;
(2) perform extraction, concentration and capture of nucleic acids;
(3) provide wash buffers and capacity to wash away inhibitory components in a given sample;
(4) enable dispensing of accurate and small volumes of multiple reagents; and
(5) provide incubation and completion of a reaction in small volumes.

The juxtaposition of large sample volume with small reaction volume allows one to conduct a wide range of diagnostics assay including a LAMP (Loop mediated isothermal amplification) based saliva test in a small, portable self-contained device.

Applications include Molecular diagnostics for health applications (including COVID19 test), Environmental Monitoring, Disease surveillance, and Veterinary health.

BRIEF DESCRIPTION OF THE DRAWINGS

FIG. 6C show an example of sample collection.
FIG. 6D shows an example of reading out a test result.

DETAILED DESCRIPTION

Figure 1:
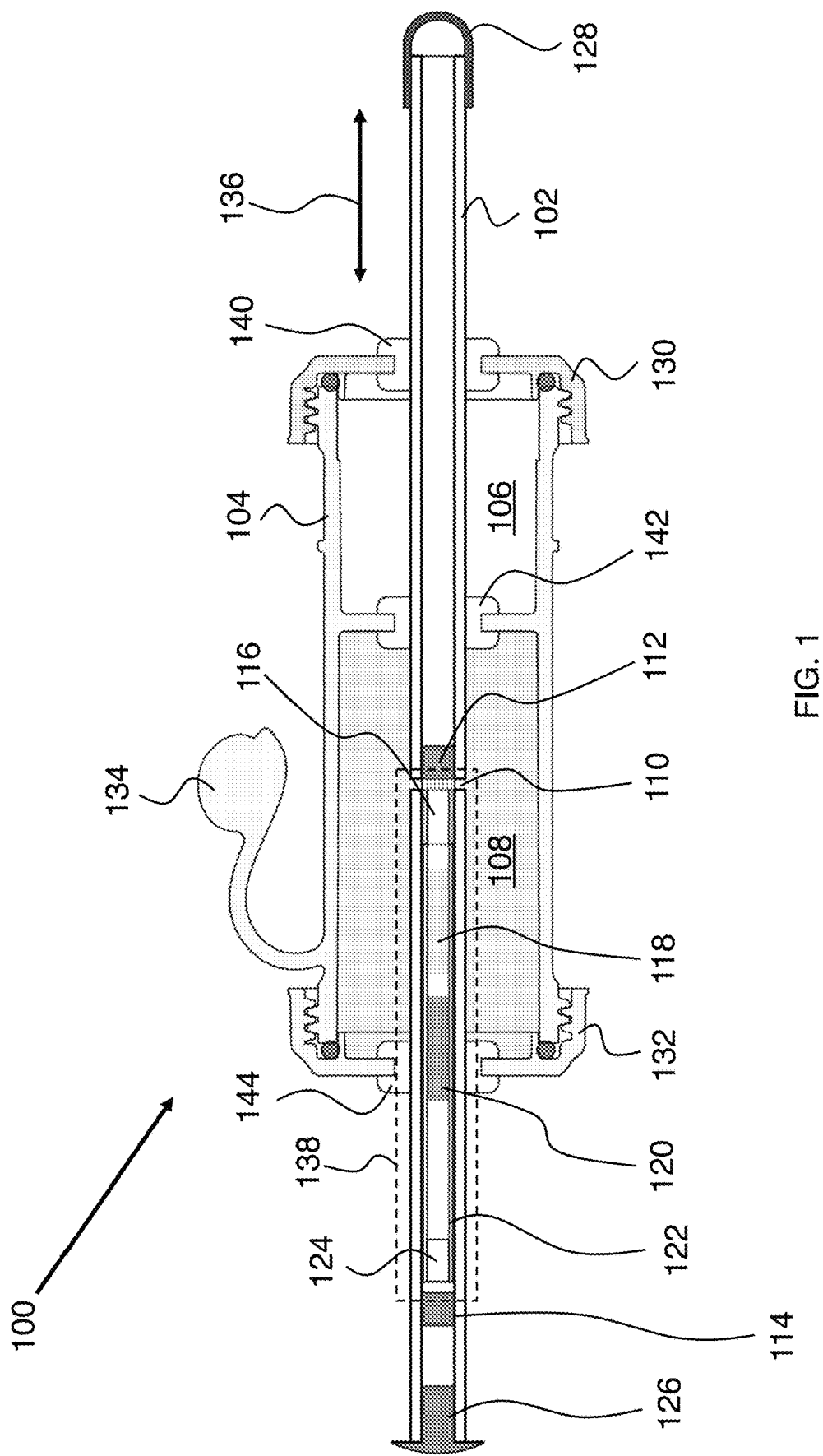
FIG. 1 shows an exemplary embodiment of the invention.

The core platform technology is based on a "coaxial" design of a plunger moving inside multiple fluid carrying/reaction zones. FIG. 1 shows an exemplary embodiment of the invention. In this example, apparatus 100 includes a hollow plunger 102 including a first seal 112 and a second seal 114 such that the first and second seals and a side wall of the plunger enclose a reaction chamber 138. Reaction chamber 138 includes a capture matrix 116 (cellulose for example) for biomolecules. Any material known in the art to be suitable for use as a capture matrix can be employed as the capture matrix.

In an initial plunger configuration (e.g., the configuration of FIG. 1 or FIG. 2A or FIG. 2B), an aperture 110 in the side wall is disposed between the first seal 112 and the second seal 114 to permit fluid to enter and leave the reaction chamber 138. For simplicity, aperture 110 is shown on the figures as a single aperture. However, one or more apertures or pores can be used to perform this function.

The apparatus includes a tube 104 disposed around the hollow plunger 102 and defining at least a sample collection chamber 106 and a sample washing chamber 108. The apparatus can further include gaskets 140, 142, 144 which allow for the fluid chambers to be separated while enabling the plunger to still move between them. The hollow plunger 102 can be moved along its axis as indicated by 136 on FIG. 1 such that the reaction chamber 138 is in fluid communication with either the sample collection chamber (FIG. 2A) or the sample washing chamber (FIG. 1, FIG. 2B) depending on a position of the hollow plunger.

In a reaction configuration of the apparatus (e.g., FIG. 2C, FIG. 3B), aperture 110 is blocked so as to seal the reaction chamber.

Reaction chamber 138 includes one or more ampules 122 containing one or more reagents, e.g., primers 118 and LAMP mastermix 120. Ampule 122 can include an ampule seal 124 at one end. The one or more reagents can be released from the one or more ampules in the reaction chamber when the apparatus is in the reaction configuration. Here 'reagents' is used in a broad sense to include reactants, primers, enzymes, catalysts etc.—i.e., anything which may need to be provided for a chemical, biological or biochemical assay. In some embodiments, plunger 102 is flexible, thereby enabling reactions to be started by bending plunger 102 so as to break ampule(s) 122, analogous to how reactions in a glow stick are started by bending the glow stick.

The apparatus can further include one or more limit stops on the hollow plunger 102 to prevent complete removal of the hollow plunger 102 from the tube 104. In the example of FIG. 1, end caps 126 and 128 can provide this capability. The device also preferably includes a clip 134 on the side—so it can be clipped to a water cup with a known height. Tube 104 can include screw-on end caps 130 and 132.

Figure 2A:
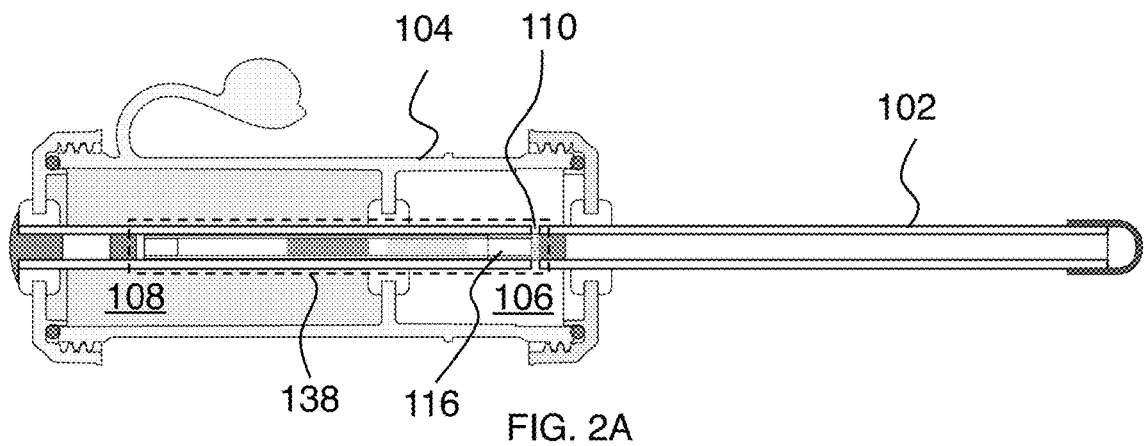
FIGS. 2A-C show operation of the example of FIG. 1.
Figure 2B:
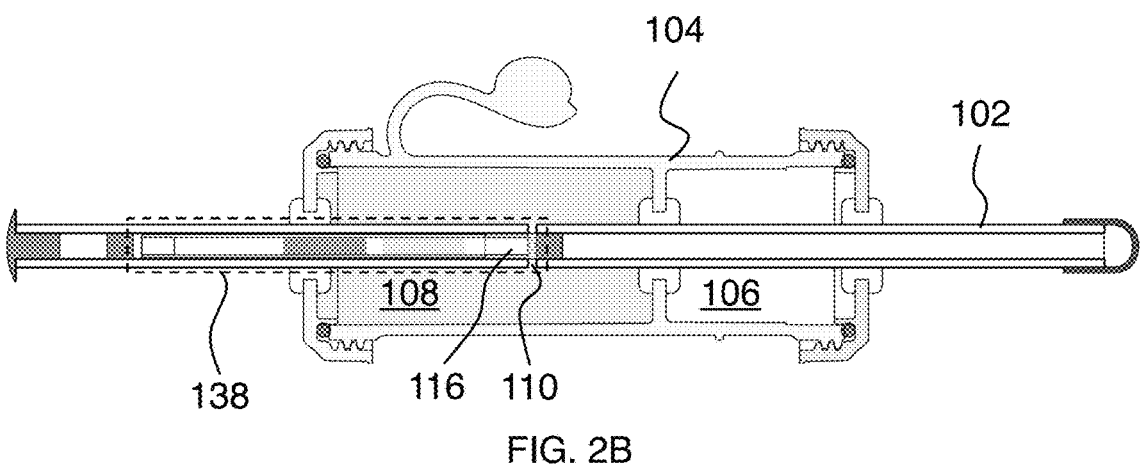
Figure 2C:
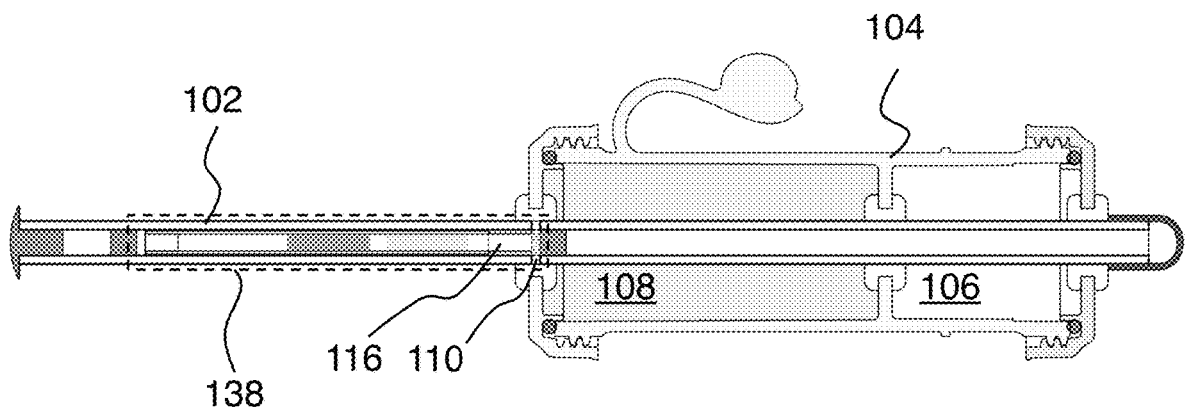

FIGS. 2A-C show according to an exemplary embodiment of the invention three positions of the device—which move the nucleic acid capture matrix 116 from one chamber (FIG. 2A, sample collection chamber) to another (FIG. 2B, sample washing chamber), thereby exposing it to various chemicals—before self-sealing it inside the plunger (FIG. 2C). In the configuration of FIG. 2C, the reaction configuration has the aperture of 110 of the hollow plunger blocked by a feature of tube 102.

User feedback can be provided to a user of the apparatus to distinguish at least two positions of the hollow plunger: a first position where the reaction chamber is in fluid communication with the sample collection chamber, and a second position where the apparatus is in its reaction configuration. In the examples of FIGS. 1 and 2A-C, this feedback is provided by the limits of motion of plunger 102 as determined by the limit stops. I.e., the user feedback is tactile feedback provided by mechanical features of the tube and hollow plunger. Alternatively, the user feedback can be visual feedback.

The one or more reagents can be released in the reaction chamber by breaking the one or more ampules.

The device has two large chambers—chamber 106 for sample collection and chamber 108 for wash buffer solution. The two chambers allow a plunger rod 102 to pass through with rubber grommets (140, 142, 144) supporting the plunger which can thus transition a nucleic acid capture material (a matrix) 116 from one chamber to another. This enables transition of material from one chamber to another while keeping the chambers sealed. Furthermore, plunger 102 itself is hollow with an internal reaction chamber 138 inside. This reaction chamber has a glass capillary 122 that contains multiple reagents as a series of droplets—with air bubbles as spacers. This allows one to store multiple chemicals in the capillary—without them ever mixing. The glass capillary 122 also has a clay-based seal 124 on one side, which traps air on one side of the ampule. This trapped air stabilizes the reagent droplets inside the glass capillary which allows for the reagents to be stored and transported inside the glass capillary with no mixing. The plunger 102 is further sealed on two ends with cylindrical seals 112, 114 while it also contains a through hole 110 making reaction chamber 138 accessible to the sample collection chamber (FIG. 2A) or the wash buffer solution (FIG. 2B). Furthermore, the hole 110 in the plunger 102 is positioned such that when the plunger is pushed all the way (FIG. 2C); it just lands right inside the rubber grommet hence sealing this chamber. This allows for the fundamental design principle—where a matrix in a small chamber is exposed to a large sample and wash chamber during first two steps; but in later steps can form a small completely sealed chamber for reaction. This juxtaposition of capturing nucleic acids from large-volume samples but running reactions at small volume is a key advantage of the device.

Figure 3A:
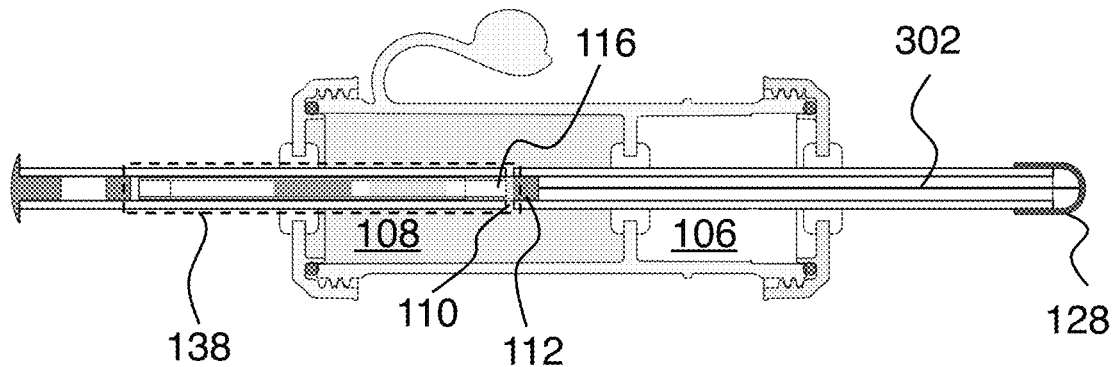
FIGS. 3A-B show an alternative way of sealing the reaction chamber.
Figure 3B:
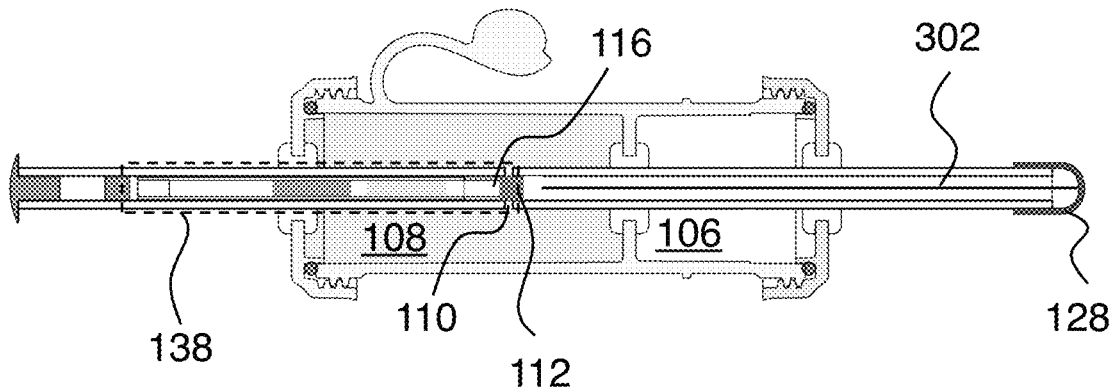

FIGS. 3A-B show an alternative way of sealing the reaction chamber 138 in the reaction configuration. In this example, the reaction configuration is formed by moving the first seal and/or the second seal within the hollow plunger such that the aperture is away from the reaction chamber. More specifically, first seal 112 is moved from a position where ii does not block aperture 110 (FIG. 3A) to a position where it blocks aperture 110 (FIG. 3B) using a push rod 302 which a user can apply force to through flexible end cap 128. Here also nucleic acids are captured from large-volume samples but reactions are run at small volumes.

When the device of FIGS. 3A-B is tapped down on a hard surface, the internal rod 302 pushes on the seal 112— moving the cellulose DNA/RNA capture matrix 116 into the chamber 138, and sealing the chamber 138 completely by moving the seal 112 to block hole 110 while simultaneously bringing all the reagents down which are mixed into the reaction chamber. This allows for high temperature incubation (60-90 degrees Celsius) for reactions without any leakage or evaporation of reagents. This tight seal ensures that the amplicons or any products further made in the reaction chamber will never be exposed to the outside world, hence avoiding any degree of contamination. This seal design also allows for the possibility of the device to be opened up without leaking any of the reaction chamber contents (for purpose of reuse and recycle).

Figure 4:
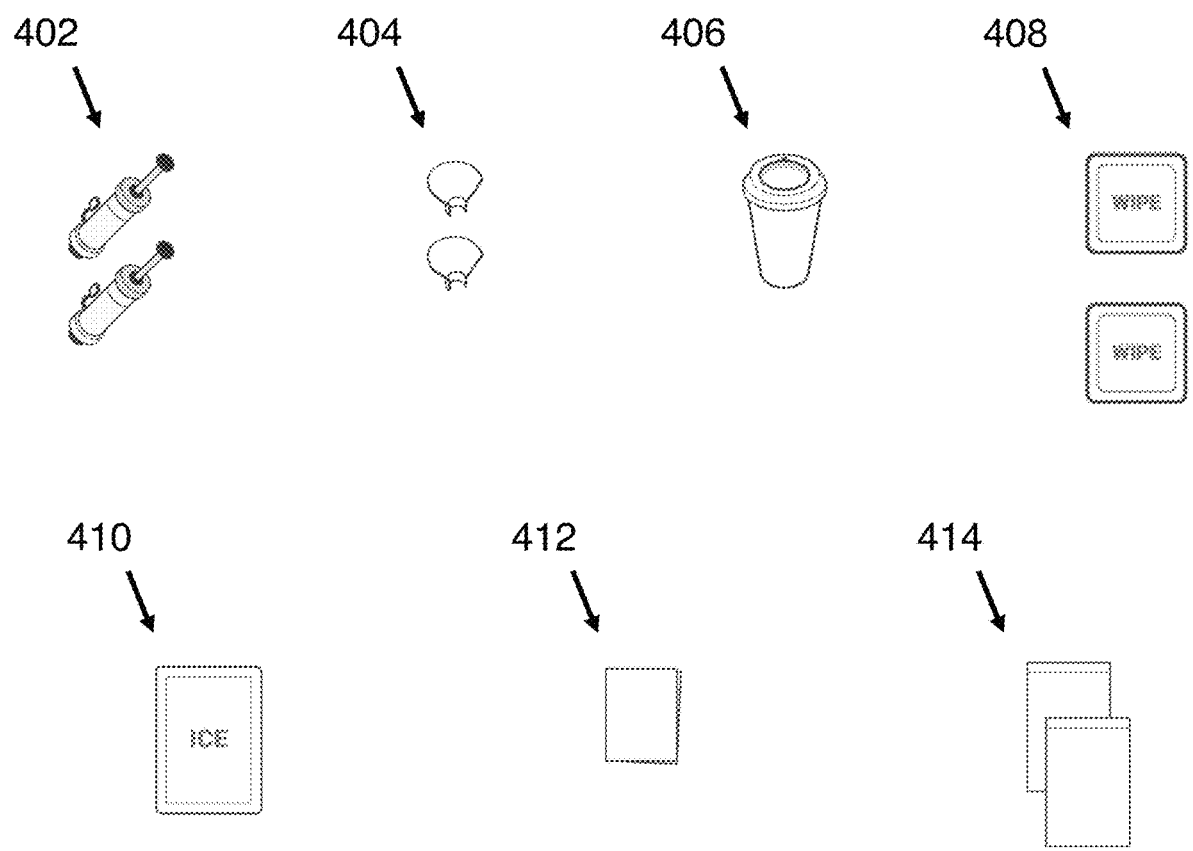
FIG. 4 shows an exemplary kit for embodiments of the invention.

FIG. 4 shows an exemplary kit for embodiments of the invention. Here 402 are two apparatuses 100 as described above, 404 are two funnels, 406 is a reusable cup with lid, 408 are two disinfectant wipes, 410 is an ice pack, 412 is an instruction packet and 414 are two empty zip lock bags. No external parts are needed other than what is listed above. The test also does not require any electricity—as long as a source of boiling water is available.

Thus an embodiment of the invention is a kit for performing biological tests, the kit including at least one test apparatus, where each test apparatus includes a hollow plunger including a first seal and a second seal such that the first and second seals and a side wall of the plunger enclose a reaction chamber, and where the reaction chamber includes a capture matrix for biomolecules.

In an initial plunger configuration, an aperture in the side wall is disposed between the first seal and the second seal to permit fluid to enter and leave the reaction chamber. The test apparatus includes a tube disposed around the hollow plunger and defining at least a sample collection chamber and a sample washing chamber.

The hollow plunger can be moved along its axis such that the reaction chamber is in fluid communication with either the sample collection chamber or the sample washing chamber depending on a position of the hollow plunger.

A reaction configuration of the test apparatus has the aperture blocked so as to seal the reaction chamber. The reaction chamber includes one or more ampules containing one or more reagents, and the one or more reagents can be released in the reaction chamber when the test apparatus is in the reaction configuration.

Such a kit can further include one or more pieces selected from the group consisting of: funnels, reusable cups with lids, disinfectant wipes, ice packs, instructions, and empty sealable plastic bags.

Figure 5:
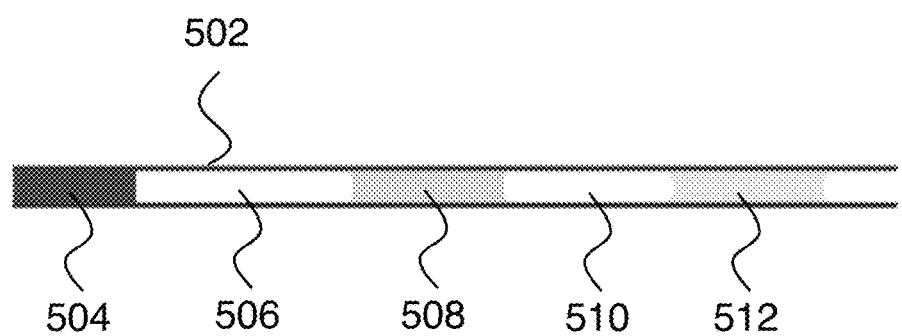
FIG. 5 shows provision of separate reagents in a single ampule.

FIG. 5 shows provision of separate reagents in a single ampule. Here the glass capillary ampule 502 has multiple liquid reagent droplets 508, 512 stored in a glass capillary; with air bubbles 506, 510 as spacers. The capillary is also sealed with clay 504 on one end—thus stabilizing the arrangement against gravity or any tilt. When the capillary is broken between the clay seal 504 and the first reagent droplet 508—this air seal is broken and liquids fall out of the capillary if it is held in vertical configuration; thereby starting the reactions.

Figure 6A:
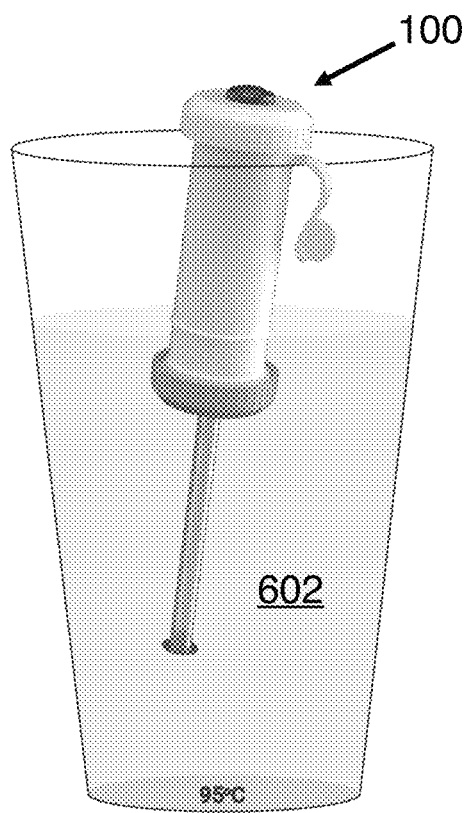
FIGS. 6A-B show temperature cycling as used in some embodiments of the invention.
Figure 6B:
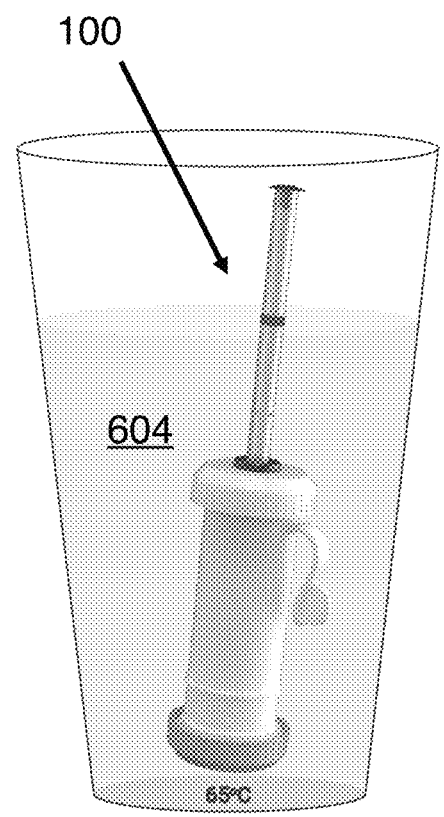

FIGS. 6A-B show temperature cycling as used in some embodiments of the invention. Here FIG. 6A shows a configuration for sample collection and sample inactivation with a high temperature (e.g., 95 C) water bath 602. FIG. 6B shows a configuration for performing a reaction (e.g., a LAMP reaction) with an intermediate temperature (e.g., 65 C) water bath 604. FIG. 6C show an example of sample collection. Here a use removes a cap, inserts a funnel and then spits into the funnel to collect the sample. FIG. 6D shows an example of reading out a test result. Here test result 610 has a visual read out where colors are different (e.g., 614 vs. 612) according to test results (e.g., positive or negative). Here different colors are schematically indicated with different line patterns. Readout of such colorimetric results can be done either by eye or by an electronic reader An exemplary operation sequence is as follows. The device is operated by first adding biological sample to sample collection chamber 106 (which can be labelled saliva chamber). The lid is aerosol tight and is closed; enabling the sample to be trapped inside fluid zones. The device is inverted and put in boiling hot water for heat inactivation (FIG. 6A)—which kills any active viral or infectious agents (e.g., 95 degrees Celsius for 3 min). With inverted geometry—only the first chamber sees the heat while the second and third chamber (including primers and enzymes) do not get heated since they are above the water line. The design can include an air jacket around the reagent capillary to ensure that the heat is not transferred to the reagents during this cycle.

After 3 minutes, the plunger 102 is pulled inwards where the DNA capture material 116 in core cylinder which has captured any DNA/RNA in the solution moves to the sample washing chamber 108 (as shown on FIG. 2B). The sample washing chamber 108 contains salt water that is "pre-filled" and hence allows for the DNA capture material to be washed and remove any unwanted agents that can hinder the reaction, including proteins present in biological samples. The chamber geometry can accommodate different volumes of salt water and hence can allow for arbitrary dilution factor. Once the plunger and DNA capture material has been soaked in the sample washing chamber 108 for sufficient time, the plunger is moved again to the reaction configuration.

During the steps of sample collection and wash buffering the design utilizes a unique principle of gas expansion in a cavity due to heat. The outside chambers 106 and 108 contain liquids and some gas—while the plunger also contains the DNA/RNA capture matrix 116 and gas. With elevated temperature at various steps—the gas in both of these chambers expands (e.g., sample collection chamber 106 and reaction chamber 138 inside the plunger in the configuration of FIG. 2A)—with a DNA/RNA capture matrix 116 acting as a plug between these two chambers. With the relative size of air being larger in the outside chamber—during a heat cycle liquid is forced inside the reaction chamber to ensure that the matrix is getting fully exposed to the sample; while during the cooling phase—since the air outside chamber is larger in volume—it contracts and pulls out any liquid that might be present in the reaction chamber, effectively running a wash cycle and drying the solid matrix. Thus, here one utilizes heat and cool cycles to bring liquids in the reaction chamber and out—without any explicit pumps or valves. The volume of these chambers is designed such that the system acts as a "self-pumping" device utilizing the heat energy of the thermal cycles. Thus, in preferred embodiments, volumes and gas/liquid ratios in the reaction chamber and the sample washing chamber are configured such that temperature cycling of the apparatus serves to drive fluid into and out of the reaction chamber due to temperature-dependent gas pressure.

After the sample and wash buffer steps, the plunger 102 moves to its final position (e.g., FIG. 2C, FIG. 6B) where the hole(s) 110 in the plunger 102 are sealed by the grommet. These pores are blocked by the last gasket and hence the core of the cylinder forms a sealed chamber. Since multiple (single) glass capillary ampule is already present in the inner plunger chamber; a simple bending of this flexible plunger allows for the glass to break and all reagents fall to the bottom of the chamber. This happens due to trapped air between clay seal and the last reagent in a train of reagents in the plunger is released—forcing the reagents to come down due to gravity. This allows for both mixing and release of reagents to the reaction vessel—and also get in contact with the DNA/RNA capture matrix. This finally begins the last step of the amplification reaction.

The device can be heated either by external heaters or with just a cup of hot water.

We have demonstrated the application of these principles by building a saliva based COVID19 home test that can be conducted using LAMP based reaction chemistry and have demonstrates the capacity to run complex chemical/analytical tests in an integrating platform. The platform is generic and enables a large number of multi-step chemistry reactions to be performed in a single integrated device.

The preceding examples of device operation relate to performing temperature cycling reactions (e.g., LAMP). However, this approach is also applicable to isothermal reactions.

The invention claimed is:

1. Apparatus for performing biological tests, the apparatus comprising:
    a hollow plunger including an axis, a side wall, an aperture in the side wall, a first seal and a second seal such that the first and second seals and the side wall of the plunger enclose a reaction chamber, wherein the reaction chamber includes a capture matrix for biomolecules;
    wherein, in an initial plunger configuration, the aperture in the side wall is disposed between the first seal and the second seal to permit fluid to enter and leave the reaction chamber;
    a tube disposed around the hollow plunger and defining at least a sample collection chamber and a sample washing chamber,
    wherein the hollow plunger can be moved along the axis such that the reaction chamber is fluidically connected with either the sample collection chamber or the sample washing chamber depending on a position of the hollow plunger;
    wherein when in a reaction configuration the aperture is blocked so as to seal the reaction chamber;
    wherein the reaction chamber includes one or more ampules containing one or more reagents;
    wherein the one or more reagents can be released from the one or more ampules in the reaction chamber when the apparatus is in the reaction configuration.

2. The apparatus of claim 1, wherein volumes and gas/liquid ratios in the reaction chamber and the sample washing chamber are configured such that temperature cycling of the apparatus serves to drive fluid into and out of the reaction chamber due to temperature-dependent gas pressure.

3. The apparatus of claim 1, wherein volumes and gas/liquid ratios in the reaction chamber and the sample collection chamber are configured such that temperature cycling of the apparatus serves to drive a sample from the sample collection chamber into the reaction chamber due to temperature-dependent gas pressure.

4. The apparatus of claim 1, wherein at least one of the one or more reagent ampules includes two or more reagents separated by one or more air bubbles such that the two or more reagents do not mix before the reagents are released.

5. The apparatus of claim 1, further comprising one or more limit stops on the hollow plunger to prevent complete removal of the hollow plunger from the tube.

6. The apparatus of claim 1, wherein when in the reaction configuration the aperture of the hollow plunger is blocked by the first seal.

7. The apparatus of claim 1, wherein the reaction configuration is formed by moving the first seal and/or the second seal within the hollow plunger such that the aperture is away from the reaction chamber.

8. The apparatus of claim 1, wherein the one or more ampules are breakable and the one or more reagents are released in the reaction chamber by breaking the one or more ampules.

9. A kit for performing biological tests, the kit comprising:
one or more pieces selected from the group consisting of: funnels, reusable cups with lids, disinfectant wipes, ice packs, instructions, and empty sealable plastic bags; and
at least one test apparatus,
wherein each of the at least one test apparatus comprises:
a hollow plunger including an axis, a side wall, an aperture in the side wall, a first seal and a second seal such that the first and second seals and the side wall of the plunger enclose a reaction chamber, wherein the reaction chamber includes a capture matrix for biomolecules;
wherein, when in an initial plunger configuration, the aperture in the side wall is disposed between the first seal and the second seal to permit fluid to enter and leave the reaction chamber;
a tube disposed around the hollow plunger and defining at least a sample collection chamber and a sample washing chamber,
wherein the hollow plunger can be moved along the axis such that the reaction chamber is fluidically connected with either the sample collection chamber or the sample washing chamber depending on a position of the hollow plunger;
wherein when in a reaction configuration the aperture is blocked so as to seal the reaction chamber;
wherein the reaction chamber includes one or more ampules containing one or more reagents;
wherein the one or more reagents can be released in the reaction chamber when each of the at least one test apparatus is in the reaction configuration.

* * * * *